United States Patent
Ueno et al.

(10) Patent No.: US 6,746,541 B2
(45) Date of Patent: Jun. 8, 2004

(54) CRYSTALLINE MIXTURE SOLID COMPOSITION AND PROCESS FOR PREPARATION THEREOF

(75) Inventors: Ryuzo Ueno, Nishinomiya (JP); Akihiko Tabata, Kawanishi (JP); Junya Honda, Nishinomiya (JP); Yojiro Furukawa, Itami (JP); Sho Arai, Nishinomiya (JP)

(73) Assignee: Kabushiki Kaisha Ueno Seiyaku Oyo Kenkyusho, Osaka (JP)

( * ) Notice: Subject to any disclaimer, the term of this patent is extended or adjusted under 35 U.S.C. 154(b) by 105 days.

(21) Appl. No.: 09/958,666

(22) PCT Filed: Feb. 14, 2001

(86) PCT No.: PCT/JP01/01027
§ 371 (c)(1),
(2), (4) Date: Oct. 12, 2001

(87) PCT Pub. No.: WO01/60831
PCT Pub. Date: Aug. 23, 2001

(65) Prior Publication Data
US 2003/0079740 A1 May 1, 2003

(30) Foreign Application Priority Data
Feb. 17, 2000 (JP) ..................... 2000-039276

(51) Int. Cl.$^7$ ............... C13F 3/00; C13F 1/02; C07H 1/00; C07H 1/06; C13K 5/00
(52) U.S. Cl. .............. 127/30; 127/29; 127/58; 127/60; 127/61; 536/1.11; 536/123.13; 536/124; 536/127
(58) Field of Search ............. 127/29, 30, 58, 127/60, 61; 536/1.11, 127, 123.13, 124

(56) References Cited

U.S. PATENT DOCUMENTS

| | | | |
|---|---|---|---|
| 4,684,720 A | | 8/1987 | Darsow et al. |
| 5,162,517 A | * | 11/1992 | Darsow ..................... 536/124 |
| 5,578,339 A | | 11/1996 | Kunz et al. |
| 6,103,894 A | * | 8/2000 | Degelmann et al. ........ 536/124 |
| 6,146,856 A | * | 11/2000 | Heikkila et al. ............ 435/100 |
| 6,180,143 B1 | * | 1/2001 | Rapp et al. .................. 426/3 |
| 6,204,378 B1 | * | 3/2001 | Duflot et al. .............. 536/125 |
| 6,414,138 B1 | * | 7/2002 | Degelmann et al. ........ 536/124 |
| 6,458,400 B1 | * | 10/2002 | Willibald-Ettle et al. ... 426/548 |
| 2002/0028276 A1 | * | 3/2002 | Rapp et al. ................. 426/548 |

FOREIGN PATENT DOCUMENTS

| | | | |
|---|---|---|---|
| EP | 0-859006 A2 | 8/1998 | |
| EP | 1172370 | * 1/2002 | ........... C07H/15/04 |
| JP | 60-181094 | 9/1985 | |
| JP | 62-148496 | 1/1987 | |
| JP | 07-051079 | 2/1995 | |
| WO | WO-00-64916 | 11/2000 | |

OTHER PUBLICATIONS

Palatinit– herstellung, technologische eigenschaften und Analytik palatinithaltiger Lebensmittel Alimenta. 19, pp. 5–16 (1980), no month available.

* cited by examiner

*Primary Examiner*—Mark L. Bell
*Assistant Examiner*—Patricia L. Hailey
(74) *Attorney, Agent, or Firm*—Sherman & Shalloway

(57) ABSTRACT

A crystalline mixture solid composition which has almost no hygroscopicity, is easy to handle and dissolve and hardly worn by abrasion, and comprises
α-D-glucopyranosyl-1,1-mannitol and
α-D-glucopyranosyl-1,6-sorbitol and may further comprise
α-D-glucopyranosyl-1,1-sorbitol in a certain case is obtained in an extremely short period of time by a power-saving and labor-saving process with a small-scale apparatus.

A composition which comprises 20 to 75 wt % of α-D-glucopyranosyl-1,1-mannitol, 23 to 70 wt % of α-D-glucopyranosyl-1,6-sorbitol and 2 to 25 wt % of α-D-glucopyranosyl-1,1-sorbitol and is in a crystalline mixture solid state or has a specific surface area of 0.07 to 0.1 m$^2$/g, and a composition which comprises 30 to 75 wt % of α-D-glucopyranosyl-1,1-mannitol, 25 to 70 wt % of α-D-glucopyranosyl-1,6-sorbitol and has a specific surface area of 0.07 to 0.1 m$^2$/g.

The above compositions are produced by a process comprising supplying a raw material, which is obtained by optionally removing trehalulose from a mixture containing isomaltulose and trehalulose produced from cane sugar through an isomerization reaction and hydrogenating into a kneader having a thin and long cooling zone together with seed crystals and discharging the obtained composition from an outlet continuously.

30 Claims, No Drawings

CRYSTALLINE MIXTURE SOLID COMPOSITION AND PROCESS FOR PREPARATION THEREOF

FIELD OF THE INVENTION

The present invention relates to a crystalline mixture solid composition which comprises
α-D-glucopyranosyl-1,1-mannitol and
α-D-glucopyranosyl-1,6-sorbitol and may further comprise
α-D-glucopyranosyl-1,1-sorbitol in a certain case and to a process for the preparation thereof.

PRIOR ART

Hydrogenated palatinose (hydrogenated isomaltulose) has been known as one of low-calorie sweeteners which do not cause a carious tooth. The hydrogenated palatinose is a mixture of two sugar alcohols, that is, an almost equimolar mixture of α-D-glucopyranosyl-1,1-mannitol (to be abbreviated as GPM hereinafter) and its isomer α-D-glucopyranosyl-1,6-sorbitol (to be abbreviated as GPS-6 hereinafter), which can be obtained by forming palatinose (isomaltulose) from cane sugar by means of a transferase and then hydrogenating the palatinose.

The hydrogenated palatinose is known as an extremely useful sweetener which exhibits an excellent sweet taste like cane sugar, has low hygroscopicity, heat resistance, acid resistance, alkali resistance, excellent processability such as tablettability and granulability, and physiological properties such as low calorie, noncariogenic properties and insulin non-irritating properties.

As the method of crystallizing the hydrogenated palatinose, H. Schiweck's report (Alimenta. 19,5–16, 1980) discloses a vacuum crystalizar process. However, this process is very complicated and repeats the steps of evaporation, aging and centrifugation, thereby consuming a huge amount of energy and boosting product costs.

JP-A 60-181094 (the term "JP-A" as used herein means an "unexamined published Japanese patent application") discloses a process for crystallizing an aqueous solution of hydrogenated palatinose having a solid content of about 80% in a vacuum crystallization apparatus. However, since this process requires a special apparatus such as a vacuum crystallization apparatus and employs a batch system, it is not practical due to its low production efficiency.

JP-A 62-148496 discloses a process for crystallizing hydrogenated palatinose in accordance with a kneading method using seed crystals. This process is used to crystallize mainly a GPM component out of hydrogenated palatinose components. That is, the water content of the hydrogenated palatinose is adjusted to a range of more than 5% and 20% or less, the liquid temperature is maintained at a range of 50 to 90° C. according to the content of water, seed crystals are added and mixed, and the mixed product is solidified by cooling the temperature at around room temperature, dried and ground to obtain crystallized hydrogenated palatinose powders. However, this process has a problem with processing (such as grindability) as the kneaded product obtained by this process has high stickiness and also a problem with distribution (such as caking and the propagation of microorganisms) as cooling and drying take long time.

It is also known that when a transferase is caused to act on cane sugar, trehalulose (α-D-glucopyranosyl-1,1-fructose) is formed in addition to isomaltulose. Generally speaking, when hydrogenated palatinose is produced, after only palatinose is obtained by crystallization separation, the residual mixture containing trehalulose is discarded or disposed at a low cost. It is known that trehalulose is converted into GPM and α-D-glucopyranosyl-1,1-sorbitol (to be abbreviated as GPS-1) by hydrogenation. That is, when a transferase is caused to act on cane sugar as a raw material and the obtained mixture is hydrogenated, a mixture of GPM, GPS-6 and GPS-1 can be obtained. To obtain such a mixture, a process is known as disclosed in JP-A 7-51079. This process comprises the first step of carrying out the conversion reaction of cane sugar, the second step of removing unreacted cane sugar and the third step of carrying out a hydrogenation reaction in the presence of a catalyst. As for solidification, the above publication discloses a fine particulate product obtained by vaporizing water for solidification and grinding. However, the product is an amorphous and glass-like solid, has high hygroscopicity, and is difficult to handle and easily worn by abrasion during circulation.

SUMMARY OF THE INVENTION

In object of the present invention to provide a crystalline mixture solid composition which has almost no hygroscopicity, is easy to handle and dissolve, and hardly worn by abrasion, comprises GPM, GPS-6 and GPS-1.

It is another object of the present invention to provide a composition which comprises GPM and GPS-6 and may further comprise GPS-1 in a certain case and has a specific surface area of 0.07 to 0.1 $m^2/g$.

It is still another object of the present invention to provide a power-saving and labor-saving process for producing the above composition of the present invention in an extremely short period of time with a small-scale apparatus.

Other objects and advantages of the present invention will become apparent from the following description.

According to the present invention, firstly, the above objects and advantages of the present invention are attained by a crystalline mixture solid composition which comprises 20 to 75 wt % of α-D-glucopyranosyl-1,1-mannitol, 23 to 70 wt % of α-D-glucopyranosyl-1,6-sorbitol and 2 to 25 wt % of α-D-glucopyranosyl-1,1-sorbitol (above weight percentages are based on the total weight of
α-D-glucopyranosyl-1,1-mannitol,
α-D-glucopyranosyl-1,6-sorbitol and
α-D-glucopyranosyl-1,1-sorbitol).

According to the present invention, secondly, the above objects and advantages of the present invention are attained by a composition which comprises 20 to 75 wt % of α-D-glucopyranosyl-1,1-mannitol, 23 to 70 wt % of α-D-glucopyranosyl-1,6-sorbitol and 2 to 25 wt % of α-D-glucopyranosyl-1,1-sorbitol and has a specific surface area of 0.07 to 0.1 $m^2/g$.

According to the present invention, thirdly, the above objects and advantages of the present invention are attained by a composition which comprises 30 to 75 wt % of α-D-glucopyranosyl-1,1-mannitol and 25 to 70 wt % of α-D-glucopyranosyl-1,6-sorbitol and has a specific surface area of 0.07 to 0.1 $m^2/g$.

Further, according to the present invention, fourthly, the above objects and advantages of the present invention are attained by a process for producing the above composition of the present invention, the process comprising the steps of:

(1) continuously supplying a raw material, which is obtained by optionally removing trehalulose from a mixture of isomaltulose and trehalulose produced from cane sugar through an isomerization reaction according to circumstances and hydrogenation into a kneader having a thin and long cooling zone together with seed crystals; and (2) discharging the reaction product from an outlet continuously.

The present invention is described in detail hereinbelow.

A description is first given of the process of the present invention.

In the process of the present invention, the crystalline mixture solid composition of the present invention is produced from a raw material obtained by hydrogenating a mixture containing isomaltulose and trehalulose produced from cane sugar through an isomerization reaction. Before hydrogenation, trehalulose may be removed. The crystalline mixture solid composition of the present invention is produced by injecting the raw material into the kneader having a thin and long cooling zone together with seed crystals.

As for the preferred ratio of isomaltulose and trehalulose before hydrogenation, the amount of isomaltulose is 5 to 100% and that of trehalulose is 0 to 95%.

The crystalline mixture solid composition of the present invention can be produced by hydrogenating a mixture containing isomaltulose and trehalulose which is produced from cane sugar through an isomerization reaction or a mixture from which trehalulose has been removed without separating impurities. After hydrogenation, if necessary crystallization or the like is carried out as required to change the ratio of the three components.

The transferase used in the isomerization may be a culture of bacteria which is generally used for the production of isomaltulose, enzyme extracted from the bacteria or immobilized product thereof. The bacteria may be the one belongs to the genuses of Protaminobacter, Serratia, Erwinia, Klebsierra, Pseudomonas, Agrobacterium and Leuconostoc.

The water content of a mixed solution which contains GPM and GPS-6 and may contain GPS-1 in a certain case as a raw material may be adjusted to a level equivalent to the water of crystallization of GPM, preferably 2 to 10 wt %, more preferably 5 to 8 wt %.

The temperature of the raw material to be supplied into the kneader may be generally a temperature at which the seed crystals do not dissolve, preferably 70 to 140° C., more preferably 90 to 130° C. in view of high fluidity for handling ease and manipulation ease for the formation of a magma.

The temperature of a cooling portion for forming a magma may be adjusted to a temperature at which generated crystallization heat can be removed, preferably 100° C. or less, more preferably 70° C. or less.

The feed rate of the raw material which differs according to the type and capacity of the kneader in use is approximately 2 to 50 kg/hr when the KRC kneader (2S) of Kurimoto Ltd. is used.

Any seed crystals may be added if the mixed solution which contains GPM and GPS-6 and may contain GPS-1 in a certain case crystallizes within the kneader. For example, crystal powders having almost the same GPM/GPS-6/GPS-1 composition as the mixed solution as the raw material or recycled crystal powders produced by the present invention may be used. The seed crystals are preferably added at a rate of 0.1 to 25 kg/hr. The amount of the seed crystals is not particularly limited but preferably 2 to 50 wt %, more preferably 5 to 40 wt % based on the raw material in view of crystallization speed and costs.

Any kneader can be used in the present invention if it is of a closed type, can knead and cool at the same time, and can continuously extrude the product from an outlet after kneading and cooing in the presence of the seed crystals. For example, an extruder, continuous kneader, mixtron, kneadex or the like is used. Out of these, an extruder is preferred. Examples of the extruder include KRC kneader (of Kurimoto Ltd.), double-screw extruder for foods (of Nippon Steel Co., Ltd.) and double-screw cooking extruder (of W & P Co. Ltd. of Germany).

To discharge a magma from the kneader, the shape of the magma can be optionally selected from noodle-like, ribbon-like, bar-like and plate-like shape sand the like. In consideration of the subsequent cooling and grinding steps, the magma is preferably discharged in a noodle-like or ribbon-like shape. A porous plate provided at the outlet preferably has a pore diameter of 2 to 5 mm and a porosity of 10 to 40%.

Although the cooling method is not particularly limited, one in which magma discharged from the kneader is directly exposed to cool air, one in which magma is left at room temperature, and one in which magma is cooled to room temperature with cool air on a metal net belt may be employed.

The obtained crystalline mixture solid composition can be made powder by grinding or granule by granulation. The grinding and granulation methods are not particularly limited and commonly used grinders and granulators are used. If required, the obtained powder and granule may be dried by a generally used drying method.

According to the above process of the present invention, the crystalline mixture solid composition of the present invention is obtained. GPM and GPS-6 contained in the composition of the present invention are existent in a crystalline state at normal temperature whereas GPS-1 is amorphous at normal temperature. Therefore, the composition of the present invention apparently shows a crystalline state but when it contains GPS-1 or the like, it is expressed in view of the above fact that the composition is in a crystalline mixture solid state.

That is, the composition of the present invention is a crystalline mixture solid composition when it comprises 20 to 75 wt % of GPM, 23 to 70 wt % of GPS-6 and 2 to 25 wt % of GPS-1. Preferably, the amount of GPM is 29.5 to 75 wt % and that of GPS-6 is 24.5 to 70 wt %. More preferably, the amount of GPM is 29.5 to 65 wt % and that of GPS-6 is 30 to 65 wt %. The amount of GPS-1 is preferably 2.8 to 25 wt %, more preferably 2.8 to 15 wt %.

A composition which comprises 30 to 75 wt % of GPM and 25 to 70 wt % of GPS-6 and does not comprise GPS-1 and has a specific surface area of 0.07 to 0.1 $m^2/g$ is in a crystalline mixture solid state. The composition of the present invention comprises GPM and GPS-6 in a total amount of preferably 80 wt % or more, more preferably 90 wt % of more based on the solid content.

The composition of the present invention is preferably uniform in particle diameter so that particles having a particle diameter of 16 to 60 Tyler mesh should account for at least 70 wt % of the total.

The specific surface area of the composition of the present invention is preferably 0.07 to 0.1 $m^2/g$, more preferably 0.075 to 0.09 $m^2/g$.

The bulk density (apparent specific gravity) of the composition of the present invention is preferably 0.7 to 0.8 g/cc, more preferably 0.73 to 0.77 g/cc.

According to the above process, there can be obtained a high-quality powdery or granular crystalline mixture solid composition which does not require a drying step, is easy to handle and dissolve, and is hardly worn by abrasion.

The following examples and comparative examples are given to further illustrate the present invention.

EXAMPLES

"%" in the following examples and comparative examples means "wt %" unless otherwise stated.

Test Example 1

5% of corn steep liquor, 2% of cane sugar, 1% of $Na_2HPO_4$, 0.15% of NaCl and 0.1% of $MgSO_4$ were dissolved in water, pH of this solution was adjusted to 7, and a strain of Serratia Plymuthica ATCC15928 was inoculated to a 500 ml Sakaguchi flask containing 100 ml of a sterilized culture medium from a storage slant and cultured by shaking in a thermostatic chamber at 30° C. for 12 hours.

As a preculture, 80 ml of this culture solution was inoculated to a 8-liter small-sized culture apparatus containing 4 liters of the above medium and cultured at 30° C. and a stirring speed of 400 rpm for 6 hours while air was blown at a rate of 4 liters per minute.

As a main culture, 3 liters of this culture solution was inoculated to a 200-liter fermentation tank containing 150 liters of the above medium and cultured at 30° C. and a stirring speed of 225 rpm for 12 hours while air was blown at 150 liters per minute.

The culture was centrifugated to collect the cells and disintegrated by a French press to obtain about 15 liters of a crude enzyme solution.

The obtained crude enzyme solution was added to a 40% cane sugar solution in an amount of 0.4% based on the cane sugar and reacted at 40° C. for 32 hours. When the reaction solution was treated with an ion exchange resin and activated carbon in accordance with a commonly used method, an isomerized cane sugar solution having the following composition was obtained.

| | |
|---|---|
| isomaltulose | 83.0% |
| trehalulose | 13.2% |
| glucose | 1.8% |
| fructose | 1.7% |
| cane sugar | 0.4% |

This isomerized cane sugar solution was hydrogenated with about 4 MPa of hydrogen gas in the presence of Raney nickel at 125° C. for 150 minutes. The composition (wt % in the solid content) of a hydride obtained by separating the nickel catalyst and purifying with activated carbon and ion exchange resin in accordance with a commonly used method was as follows.

| | |
|---|---|
| GPM | 58.4% |
| GPS-6 | 33.9% |
| GPS-1 | 2.7% |
| sorbitol | 1.7% |
| mannitol | 0.7% |
| other sugars and sugar alcohols | 2.7% |

(As for the proportion of each component to the total weight of GPM, GPS-6 and GPS-1, the amount of GPM was 61.5 wt %, that of GPS-6 was 35.7 wt % and that of GPS-1 was 2.8 wt %.)

Example 1

The hydride obtained in the Test Example 1 was concentrated to a water content of about 6%, and this solution was injected into a continuous kneader provided with a porous plate having a large number of 5 mm diameter round holes at an outlet (S2-KRC kneader of Kurimoto Tekkojo KK, jacket temperature of 10° C., revolution of 60 rpm) at a rate of 12.6 kg/hr while it was kept at 120° C. Seed crystals were injected at a rate of 5.4 kg/hr at the same time. The seed crystals were obtained by grinding commercially available hydrogenated isomaltulose (trade name: ISOMALT Type M, purchased from Parachinit Co., Ltd., spherical solid containing about 52.3% of GPM and about 47.1% of 1,6-GPS based on the solid content and having a diameter of 0.5 to 4.5 mm) and putting the ground product through a sieve to obtain particles of 60 mesh or less and recycled when they became steady. As a result, a noodle-like product discharged from the porous plate was exposed to cool air to be solidified by cooling to obtain easily a crystalline mixture solid composition. The obtained crystalline mixture solid composition had no stickiness, can be easily made uniform in size by a grinder, does not need to be dried and can be used directly for various purposes.

Example 2

A crystalline composition was produced in the same manner as in Example 1 except that commercially available hydrogenated isomaltulose (trade name: ISOMALT Type M, purchased from Parachinit Co., Ltd., spherical solid containing about 52.3% of GPM and about 47.1% of 1,6-GPS and having a diameter of 0.5 to 4.5 mm) whose water content was adjusted to about 6% after it was molten by heating was used as a raw material. The same seed crystals as in Example 1 were used. As a result, a crystalline composition which had no stickiness and was easily processed was obtained as in Example 1.

Comparative Example 1

A test was carried out in accordance with the method described in Example 6 of JP-A 7-51079 using the same raw material as in Example 1 as follows.

The raw material whose water content was concentrated to about 6% was poured into a stainless steel tray (thickness of about 7 mm), left at room temperature for one night and solidified, and the solidified product was broken by a hammer to obtain a crystalline mixture solid composition. This was a transparent glass-like solid which had high stickiness and hygroscopicity and accordingly had a handling problem.

Comparative Example 2

A test was carried out in accordance with the method described in Example 2 of JP-A 62-148496 using the same raw material as in Example 2 as follows.

A solution having a water content of about 10% was obtained by melting the raw material by heating and adjusting its water content. 500 g of this solution heated at 75° C. was injected into a 2-liter twin-arm batch kneader (jacket temperature of 75° C.) together with 50 g of seed crystals and kneaded. In about 8 minutes after the start of kneading, the kneaded product became plasticized, taken out on a vat, fully cooled with cool air and broken by a hammer to obtain small pieces. They were dried at 50° C. for one night to obtain a crystalline composition (water content after drying: 5.4%). However, as the kneaded product had high stickiness and took long to be cooled, it was inferior in handling ease.

Example 3

The crystalline mixture solid compositions obtained in Example 1 and Comparative Example 1, the crystalline compositions obtained in Example 2 and Comparative Example 2 and commercially available hydrogenated isomaltulose were ground and put through a sieve to obtain a uniform particle size of 16 to 60 mesh (16 to 22 mesh only when the dissolution speed was measured) and the physical properties of the obtained products were compared with one another according to the following criteria. Each value is a mean value of several measurement data.

Specific Surface Area

After a sample was dried at room temperature for 1 hour and further vacuum dried at 50° C. in Monosobe MS-17 (Yuasa Ionics Co., Ltd.) for 15 minutes, the specific surface area of this sample was measured.

Amount of Absorbed Oil 25 g of a sample and an appropriate amount of partially hydrogenated rapeseed oil were mixed together and left for 5 minutes, oil not held by a centrifugal machine with a 60 M net was removed (620G, 10 min.), and the weight (A) of the sample containing the residual oil was measured. The oil absorption rate was calculated from this value according to the following equation.

$$\text{amount of absorbed oil} = (A-25)/25 \times 100$$

Bulk Density (Apparent Specific Gravity)

This was measured using the powder tester PT-N (of Hosokawa Micron Co., Ltd.) (number of times of tapping: 180).

Dissolution Speed 250 g of about 8° C. water was placed in a 300 ml beaker and 5 g of a sample was added under agitation with a stirrer having 3 agitation wings (400 rpm) to measure the time elapsed until the sample dissolved in water.

Degree of Abrasion Wear 15 g of a sample was placed in a Meyer equipped with a 500 ml baffle and shaken by a shaker (190 rpm) for 60 hours. This treated product was taken out and put through a sieve to measure the weight (B) of a fraction of 60 mesh or more. The degree of abrasion wear was measured from this value according to the following equation.

$$\text{degree of abrasion were } (\%) = (15-B)/15 \times 100$$

The results are shown in Table 1.

TABLE 1

|  | Ex. 1 | Ex. 2 | Comp. Ex. 1 | Comp. Ex. 2 | Commercial product |
|---|---|---|---|---|---|
| specific surface area (m²/g) | 0.081 | 0.087 | 0.068 | 0.3 | 0.068 |
| amount of absorbed oil (%) | 4.12 | 3.72 | 4.12 | 9.2 | 2.32 |
| bulk density (g/cc) (apparent specific gravity) | 0.74 | 0.77 | 0.78 | 0.74 | 0.85 |
| dissolution speed (sec) | 133 | 146 | 98 | 171 | 173 |
| degree of abrasion wear (%) | 0.7 | 1 | 6.5 | 2.1 | 1.1 |

Ex.: Example
Comp. Ex.: Comparative Example

Effect of the Invention

According to the present invention, a crystalline mixture solid composition which has almost no hygroscopicity, is easy to handle and dissolve and hardly worn by abrasion, and comprises α-D-glucopyranosyl-1,1-mannitol and α-D-glucopyranosyl-1,6-sorbitol and may further comprise α-D-glucopyranosyl-1,1-sorbitol in a certain case is obtained in an extremely short period of time by a power-saving and labor-saving process with a small-scale apparatus.

What is claimed is:

1. A crystalline mixture solid composition which comprises 20 to 75 wt % of α-D-glucopyranosyl-1,1-mannitol, 23 to 70 wt % of α-D-glucopyranosyl-1,6-sorbitol and 2 to 25 wt % of α-D-glucopyranosyl-1,1-sorbitol (the above weight percentages are based on the total weight of α-D-glucopyranosyl-1,1-mannitol, α-D-glucopyranosyl-1,6-sorbitol and α-D-glucopyranosyl-l, 1,1-sorbitol).

2. The composition of claim 1 which comprises 29.5 to 75 wt % of α-D-glucopyranosyl-1, 1-mannitol and 24.5 to 70 wt % of α-D-glucopyranosyl1,6 sorbitol.

3. The composition of claim 2 which comprises 2.8 to 25 wt % of α-D-glucopyranosyl-1,1-sorbitol.

4. The composition of claim 1 which has a specific surface area of 0.07 to 0.1 m²/g.

5. The composition of claim 1, wherein particles of 16 to 60 Tyler mesh account for at least 70 wt % of the total.

6. The composition of claim 1 which has a bulk density (apparent specific gravity) of 0.7 to 0.8 g/cc.

7. The composition of claim 1 which comprises 2.8 to 25 wt % of α-D-glucopyranosyl-1,1-sorbitol.

8. The composition of claim 1 which comprises 2 wt % or more and less than 2.8 wt % of α-D-glucopyranosyl-1,1-sorbitol.

9. The composition of claim 1 which comprises 2 wt % or more and less than 2.8 wt % of α-D-glucopyranosyl-1,1-sorbitol.

10. A composition which comprises 30 to 75 wt % of α-D-glucopyranosyl-1,1-mannitol and 25 to 70 wt % of α-D-glucopyranosyl-1,6 sorbitol and has a specific surface area of 0.07 to 0.1 m2/g.

11. A composition which comprises 20 to 75 wt % of α-D-glucopyranosyl-1,1-mannitol, 23 to 70 wt % of α-D-glucopyranosyl-1,6 sorbitol and 2 to 25 wt % of α-D-glucopyranosyl-1,1 sorbitol and has a specific surface area of 0.07 to 0.1 m2/g.

12. The composition of claim which comprises 30 to 75 wt % of α-D-glucopyranosyl-1,1-mannitol, and 25 to 70 wt % of α-D-glucopyranosyl-1,6 sorbitol.

13. The composition of claim 12 which comprises 2.8 to 25 wt % of α-D-glucopyranosyl-1,1-sorbitol.

14. The composition of claim 12 which comprises 2 wt % or more and less than 2.8 wt % of α-D-glucopyranosyl-1, 1-sorbitol.

15. The composition of claim 1 which comprises 2.8 to 25 wt % of α-D-glucopyranosyl-1,1-sorbitol.

16. The composition of claim 11 which comprises 2 wt % or more and less than 2.8 wt % of α-D-glucopyranosyl-1, 1-sorbitol.

17. A crystalline mixture solid composition which comprises more than 70 wt % and 75 wt % or less of α-D-glucopyranosyl-1,1-mannitol, 23 to 28 wt % of α-D-glucopyranosyl-1,6-sorbitol and 2 to 7 wt % of α-D-glucopyranosyl-1,1-sorbitol.

18. A composition which comprises more than 70 wt % and 75 wt % or less of α-D-glucopyranosyl-1,1-mannitol, 23 to 28 wt % of α-D-glucopyranosyl-1,6-sorbitol and 2 to 7 wt % of α-D-glucopyranosyl-1,1-sorbitol and has a specific surface area of 0.07 to 0.1 m²/g.

19. A process for producing a composition comprising the steps of supplying a raw material, which is obtained by hydrogenating a mixture containing isomaltulose and trehalulose produced from cane sugar through an isomerization reaction, optionally after removing trehalulose from the mixture, into a kneader having a cooling zone together with seed crystals and discharging the obtained composition from an outlet continuously, said obtained composition being a crystalline mixture solid composition which comprises 20 to 75 wt % of α-D-glucopyranosyl1,1-mannitol, 23 to 70 wt % of α-D-glucopyranosyl-1,6-sorbitol and 2 to 25 wt % of α-D-glucopyranosyl-1,1-sorbitol.

20. The process of claim 19, wherein the mixture containing isomaltulose and trehalulose is directly hydrogenated without separating impurities.

21. The process of claim 19, wherein the amount of isomaltulose is 5 to 100% and the amount of trehalulose is 0 to 95%.

22. A process for producing a composition comprising the steps of supplying a raw material, which is obtained by hydrogenating a mixture containing isomaltulose and trehalulose produced from cane sugar through an isomerization reaction, optionally after removing trehalulose from the mixture, into a kneader having a cooling zone together with seed crystals and discharging the obtained composition from an outlet continuously, said obtained composition being a composition which comprises 20 to 75 wt % of α-D-glucopyranosyl-1,1-mannitol, 23 to 70 wt % of αD-glucopyranosyl1,6-sorbitol and 2 to 25 wt % of α-D-glucopyranosyl-1,1-sorbitol and has a specific surface area of 0.07 to 0.1 m$^2$/g.

23. The process of claim 22, wherein the mixture containing isomaltulose and trehalulose is directly hydrogenated without separating impurities.

24. The process of claim 22, wherein the amount of isomaltulose is 5 to 100% and the amount of trehalulose is 0 to 95%.

25. A process for producing a composition comprising the steps of supplying a raw material, which is obtained by hydrogenating a mixture containing isomaltulose and trehalulose produced from cane sugar through an isomerization reaction, optionally after removing trehalulose from the mixture, into a kneader having a cooling zone together with seed crystals and discharging the obtained composition from an outlet continuously, said obtained composition being a composition which comprises 30 to 75 wt % of α-D-glucopyranosyl-1,1-mannitol, and 25 to 70 wt % of α-D-glucopyranosyl-1,6-sorbitol and has a specific surface area of 0.07 to 0.1 m2/g.

26. The process of claim 25, wherein the mixture containing isomaltulose and trehalulose is directly hydrogenated without separating impurities.

27. The process of claim 25, wherein the amount of isomaltulose is 5 to 100% and the amount of trehalulose is 0 to 95%.

28. A crystalline mixture solid composition produced by a process comprising the steps of supplying a raw material, which is obtained by hydrogenating a mixture containing isomaltulose and trehalulose produced from cane sugar through an isomerization reaction, optionally after removing trehalulose from the mixture, into a kneader having a cooling zone together with seed crystals and discharging the obtained composition from an outlet continuously, said crystalline mixture solidcomposition comprising 20 to 75 wt % of α-D-glucopyranosyl-1,1-mannitol,23 to 70 wt % of α-D-glucopyranosyl-1,6-sorbitol and 2 to 25 wt % of α-D-glucopyranosyl-1,1-sorbitol.

29. A composition produced by a process comprising the steps of supplying a raw material, which is obtained by hydrogenating a mixture containing isomaltulose and trehalulose produced from cane sugar through an isomerization reaction, optionally after removing trehalulose from the mixture, into a kneader having a cooling zone together with seed crystals and discharging the obtained composition from an outlet continuously, said composition comprising 20 to 75 wt % of α-D-glucopyranosyl-1,1-mannitol, 23 to 70 wt % of α-D-glucopyranosyl-1,6-sorbitol and 2 to 25 wt % of α-D-glucopyranosyl-1,1-sorbitol and has a specific surface area of 0.07 to 0.1 m2/g.

30. A composition produced by a process comprising the steps of supplying a raw material, which is obtained by hydrogenating a mixture containing isomaltulose and trehalulose produced from cane sugar through an isomerization reaction, optionally after removing trehalulose from the mixture, into a kneader having a cooling zone together with seed crystals and discharging the obtained composition from an outlet continuously, said composition comprising 30 to 75 wt % of α-D-glucopyranosyl-1,1-mannitol, 25 to 70 wt % of α-D-glucopyranosyl-1,6-sorbitol and has a specific surface area of 0.07 to 0.1 m2/g.

* * * * *